(12) United States Patent
Hing et al.

(10) Patent No.: US 8,879,792 B2
(45) Date of Patent: Nov. 4, 2014

(54) MICROSCOPY METHOD FOR IDENTIFYING BIOLOGICAL TARGET OBJECTS

(71) Applicant: Sensovation AG, Radolfzell (DE)

(72) Inventors: Paul Hing, Owingen-Billafingen (DE); Stefan Bickert, Uberlingen (DE)

(73) Assignee: Sensovation AG, Radolfzell (DE)

(*) Notice: Subject to any disclaimer, the term of this patent is extended or adjusted under 35 U.S.C. 154(b) by 215 days.

(21) Appl. No.: 13/679,798

(22) Filed: Nov. 16, 2012

(65) Prior Publication Data

US 2013/0121530 A1 May 16, 2013

(30) Foreign Application Priority Data

Nov. 16, 2011 (DE) .......................... 10 2011 055 426

(51) Int. Cl.
*G06K 9/00* (2006.01)
*G06K 9/32* (2006.01)
*G01N 21/64* (2006.01)
*H04N 7/18* (2006.01)

(52) U.S. Cl.
CPC .......... *G06K 9/3241* (2013.01); *G06K 9/00134* (2013.01); *G01N 21/6458* (2013.01); *G01N 21/6486* (2013.01); *H04N 7/18* (2013.01)
USPC ............................................ 382/103; 348/79

(58) Field of Classification Search
CPC ................................... G06K 9/00; H04N 7/18
USPC ............ 382/103, 107, 236; 348/79, 169, 170, 348/171, 172, 352
See application file for complete search history.

(56) References Cited

U.S. PATENT DOCUMENTS 6,287,765 B1 * 9/2001 Cubicciotti .................. 435/6.11

FOREIGN PATENT DOCUMENTS

| DE | 69021650 T2 | 3/1996 |
| DE | 20321352 U1 | 1/2007 |
| JP | 7294822 A | 11/1995 |
| JP | 2003315678 A | 11/2003 |
| JP | 2007163553 A | 6/2007 |
| JP | 2008139708 A | 6/2008 |
| WO | 2006133899 A2 | 12/2006 |

* cited by examiner

Primary Examiner — Abolfazl Tabatabai (57) ABSTRACT

The invention relates to a microscopy method for identifying target objects (32) having a predetermined optical property in material (6) to be analyzed.

According to the invention, in a first step an overview field of view (36) of a microscope optical system (14) is directed to an overview region of a sample carrier (4) containing the material (6) to be analyzed, the material (6) to be analyzed is illuminated by an illumination unit (16), which irradiates the sample carrier (4) from outside a field of view tube (48), and is recorded by a camera (8), the material (6) to be analyzed is optically analyzed for the optical property such that even a single target object (32) having the predetermined optical property is identified as such in the material (6) to be analyzed, in a subsequent second step a target field of view (52) of the microscope optical system (14) is aligned with a target region around the target object (32) using the known position of the target object (32), and the identified target object (32) is analyzed in a differentiated manner for various additional optical properties.

17 Claims, 5 Drawing Sheets

MICROSCOPY METHOD FOR IDENTIFYING BIOLOGICAL TARGET OBJECTS

The invention relates to a microscopy method for identifying target objects, in particular biological target objects, which have a predetermined optical property, in a material to be examined.

In medical diagnostics, the identification of individual cells having a particular property in an environment of an extremely large number of similar cells is increasingly gaining in importance. One example in which the identification of individual cells plays an important role is cancer diagnostics. When blood is analyzed for cancer identification, several milliliters of blood are analyzed as to whether one or more cancer cells are present in the sample. So in extreme cases, a single cancer cell must be identified in an environment of approximately $10^8$ "normal" blood cells.

So as to be able to identify individual cells, these are typically labeled. For this purpose, such a cell is tagged with one or more markers which are tailored to the properties of this cell and indicate these very properties. Customarily fluorescent markers are used, which when irradiated with light having an excitation wavelength in turn emit light at an emission wavelength, based on which they can be uniquely identified.

Several different methods are known for identifying individual labeled cells in a blood sample. In digital microscopy, the blood is spread on a sample carrier and microscopically analyzed. The accordingly labeled cells are detected based on the special radiation characteristics thereof and are microscopically analyzed for additional properties, such as for several different markers, for example. This method has the advantage that the cells can be reliably and individually identified in the blood sample and further analyzed. However, the drawback is the duration of such an analysis. An analysis of a sample containing approximately $10^8$ cells, during which a single labeled cells is to be reliably found, is typically estimated to last several days of microscopic analyses.

Flow cytometry is a considerably faster method. In this method, the blood sample flows through a very thin capillary which is illuminated with laser light. Labeled cells that pass by are identified as such and can be counted. It is possible to achieve analysis rates of up to 150,000 cells per second, and the analysis of approximately $10^8$ cells therefore does not last any longer than 20 minutes. However, the drawback of these methods is that the analyzed cells cannot be analyzed in greater detail, but instead are "lost" in a lower collection container.

It is the object of the present invention to provide a microscopy method for identifying cells, by means of which individual cells having a predetermined optical property can be found in a relatively large quantity of material to be analyzed and can subsequently be analyzed in greater detail, wherein a method that can be carried out expeditiously is aspired.

This object is achieved by a microscopy method of the type mentioned above, in which according to the invention in a first step an overview field of view of a microscope optical system is directed to an overview region of a sample carrier containing the material to be analyzed;
the material to be analyzed is illuminated by an illumination unit, which irradiates the sample from outside a field of view tube, and is recorded by a camera;
the material to be analyzed is optically analyzed for the optical property such that even a single target object having the predetermined optical property is identified as such in the material to be analyzed;
in a subsequent second step, a target field of view of the microscope optical system is aligned with a target region around the target object using the known position of the target object;
the identified target object is analyzed in a differentiated manner for various additional optical properties; and in particular
the target object is classified in at least one of several target object classes.

The material to be analyzed is advantageously a biological material. The target objects are advantageously biological target objects. Hereinafter thus biological material and biological target objects are mentioned, without the method according to the invention being limited to these.

The method combines the advantages of classic flow cytometry with those of digital microscopy. Flow cytometry allows a high speed of the analysis to be achieved because the flowing sample is illuminated with high intensity by the acting laser radiation per unit area. The method can operate accordingly quickly. By translating the idea of the strong illumination to digital microscopy, the same can also be expedited.

A fast analysis, in conjunction with a possible subsequent thorough analysis, however, is only possible if the digital microscopy method is broken down into a two-step method, with the strong illumination being applied in the first step. The two-step method includes, in a first step, expeditiously analyzing the entire sample region to be analyzed using relatively low microscopic magnification.

Because a rapid identification of individual cells in a relatively large overview field of view is only possible with strong illumination, advantageously a strong light source is employed in the first step. By using a light source which irradiates the sample from outside the field of view tube, high illumination power per unit area can be bundled on the overall field of view which, from a microscopic view is admittedly relatively large, but from a macroscopic view is still small.

The invention is further based on the deliberation that the cell diagnostics known from the known digital microscopy field is to be broken down to the two steps so as to allow a detailed analysis. The first step thus focuses on identifying the target object as such in the mass of the biological material. In the first step, no further diagnostic analysis must be conducted. This is not carried out until the second step, so that the identified target object can be differentiated and classified.

By breaking down the identification and further diagnostics to the two steps, the illumination can be optimized in both steps to the respective task of these individual steps. In the first step, for example, the illumination selected can be optimized to the cell identification. In the first step, for example, the monochromatic irradiation is done at a frequency which is particularly suitable for cell identification, but makes any further analysis very difficult, if not impossible. In the second step, the illumination that is employed can one that is suitable for differentiation and classification, however which would make it difficult to carry out the initial identification under some circumstances, or would make it very time-consuming to do. Depending on use, it may, in some circumstances, also be possible to employ the same illumination or the same illumination source in the two steps
optionally with differing radiant powers or radiation frequencies.

The method according to the invention can be applied particularly advantageously for identifying individual and rare cells, using what is known as the rare cells detection method. In this method, which is commonly employed for diagnostics, individual and rarely occurring cells are analyzed in a large population of "normal" cells. Examples include the quantification of tumor cells in the blood or bone marrow, prenatal diagnostics, or tumor monitoring or treatment monitoring. Another advantageous field of application is the identification of free tumor cells in the bloodstream, known as Circulating Tumor Cells (CTC) detection. Individual tumor cells that have dissociated from the primary tumor and found their way into the bloodstream, either directly or after transit in lymphatic channels, pose the great risk of the formation of metastases. So as to reliably identify the risk, and in the best case even potential sites, of such metastases, this method searches for these individual circulating tumor cells. A further application example is the identification of settling tumor cells, which is known as the diagnostic Disseminated Tumor Cells (DTC) method. This method analyses tissue, for example liver tissue, bone marrow or lung tissue, in which an accumulation of formerly circulating tumor cells is suspected to have settled at the tissue site in question and begun or favored the formation of metastases.

However other, in particular medical, fields are conceivable and advantageous, in which the method according to the invention can prove the superiority thereof. Generally speaking, in clinical diagnostics the field of blood analyses can benefit from the method according to the invention, such as the testing for infections or blood diseases, for example. In pharmaceutical research, the method can be used for active ingredient screening, toxicology or efficiency analyses of active ingredients. Further fields of application include, for example, neurobiology, where the method can be employed for cell differentiation or for monitoring cell growth (ion influx). The biological target objects could be cells. The method can advantageously also be applied to other organisms. The target objects can, for example, also be cell clusters, bacteria, colonies or other organisms. Other biological target objects from medical diagnostics, such as the so-called nanocodes, are also conceivable and advantageous. The biological target objects can also be predominantly non-biological. The nanocodes, for example, carry biological material only in a small surface area, with the predominant part being the non-biological code part. It is also possible for the biological target objects to at first contain no biological material, and to not contain biological material until the second step. The same also applies to the biological material surrounding the biological target objects.

The microscopy method is advantageously a medical microscopy diagnostic method for identifying individual diagnostic objects. The sample carrier is advantageously thus a glass sample carrier, as it is used in medical diagnostics. What is known as a micro-plate is particularly advantageous, comprising several vessel regions which are separated from each other and can be analyzed individually. A suitable example of such a micro-plate is what is known as a microtiter plate measuring 128 mm×86 mm. Plates having a credit card format of 85 mm×54 mm are also common in medical diagnostics. The overview field of view can thus cover the entire sample region, which is to say a micro-plate, for example, however sub-regions are possible, which are successively scanned.

Advantageously a microscope comprising a microscope optical system and a field of view tube is used to carry out the method. The microscope optical system advantageously contains several objectives so as to allow various magnifications. The field of view tube is advantageously a tube which is disposed between such an objective and the camera and through which the optical path imaging the sample is guided toward the camera. The tube is used to improve the optical properties of the microscope, for example the option of using longer focal lengths and blocking scattered radiation. The field of view tube advantageously has a length of at least 10 cm and at least one aperture disposed in the tube for screening off scattered radiation.

The overview field of view is imaged by the microscope optical system onto an image area of the camera. The corresponding imaging beam path runs through the field of view tube, so that the optical axis of the beam path also extends through the field of view tube. Apart from the fact that the first light source is disposed outside the field of view tube, the beam path of the illuminating beams advantageously also runs entirely outside the field of view tube, which is to say not through the objective. The beam path of the illuminating beams advantageously runs from the light source to the sample carrier entirely outside the field of view tube and a microscope objective. Advantageously irradiation takes place obliquely relative to the sample surface, as incident light if possible. This arrangement of the light source or of the illuminating beam path allows very strong incident lighting, wherein the scattered radiation within the microscope can be kept at a very low level. Low emission of a marker from the biological target object can thus be identified separately from the scattered radiation, despite the strong illumination that is advantageous for expeditiously carrying out the method.

In the second step, the target field of view of the microscope optical system, which is to say advantageously of a microscope objective, is aligned with the target region around the target object. The magnification of the target field of view can be greater than that of the overview field of view. When the microscope objective is aligned with the target field of view, location information of the target object from the first step is processed. In the first step, for example, advantageously the position of an identified target object was detected and stored, advantageously in the form of two-dimensional location information. Using this known position, the target region is now controlled by the microscope optical system in a targeted manner, advantageously in an automated and motor-driven manner.

After the optical system has been aligned with the target field of view, the target object can be analyzed in a more differentiated manner, for example using greater magnification, than was already done in the first step. In the second step, for example, the target object is analyzed for additional and different optical properties, which are generated by differentiated markers, for example. However, it is also possible to carry out shape analyses of the target object, notably when analyzing nanocodes, however morphological analyses are also possible. These analyses as well are advantageously carried out in an automated fashion, wherein different classes are advantageously categorized. The optical properties are advantageously machine-readable and machine-classifiable, so that the found biological target object can automatically be assigned to one of several target object classes.

The target object can inherently exhibit the optical properties, for example as morphological properties. However, it is particularly advantageous to artificially generate the optical properties, for example by way of a marker, such as fluorescent marker. An optical property, for example a marker of the biological target objects, can be artificially generated before, during or after the first step. It is easiest to generate artificial optical properties before starting the method according to the invention. However, it is also possible to generate or modify an optical property between the steps, for example, so as to allow more detailed analyses in the subsequent step. It is also possible, and under some circumstances advantageous, to generate or modify an optical property during an analysis, in particular during the second step. For example, markers can be modified or added—in particular based on requirements, which is to say advantageously depending on previously determined analytical results. Especially with morphological analyses, the optical property may change or evolve, for example due to the administration of an active ingredient.

The markers can be fluorescent markers, luminescent markers, silver stains or colorimetric markers, for example for genes, nucleic acids, proteins in cells, cell bodies or receptors or the like. A combination of different markers for the two steps is also possible.

The analysis of the target object in the second step can be carried out using a different magnification and/or a different optical method. The target field of view, for example, can have a magnification by at least a factor of 3, and more particularly a factor of 5, over the overview field of view, whereby a more precise analysis of the previously found target object is facilitated.

If the target object is identified in the first step by means of a first optical method and the target object is differentiated in the second step by means of a second optical method which is different from the first, the two methods can be optimally tailored to the different tasks of identification and differentiation.

In a further advantageous embodiment of the invention, the material to be analyzed is illuminated by a second and different light source in the second step. This light source may be optimized for an analysis in the second step, so that the two different light sources are tailored to different tasks in the two steps. It is advantageous for the second light source to allow a differentiation of the target objects according to different further optical properties by illumination at different frequencies. It is thus possible, for example, to identify different markers, and it is possible to distinguish a variety of different properties using possible marker permutations.

It is particularly advantageous for the material in the first step to be exposed to monochrome illumination from the first light source. The term 'monochrome' shall be understood to mean a spectrum with a wavelength range of less than 50 nm, and more particularly less than 30 nm. This allows high radiant power per unit area and frequency range to be generated, which in turn allows fast identification of the individual cells. Because no differentiation and classification need to be carried out in the first step, this spectrum is advantageous for finding the cells using specialized light.

In contrast, it is advantageous for the biological material to be exposed to polychrome illumination from the second light source in the second step. This allows for easy differentiation, for example by way of excitation at different frequencies, in particular with fluorescent markers, and makes it easy to carry out. To this end, the second light source can have a continuous spectrum or several discrete frequency ranges, which are separated from each other by substantially radiation-free gaps.

Especially a light source containing LED light is suited as the first radiating element. This allows monochrome light to be generated easily and with high intensity, and especially in a way that generates relatively little heat loss.

In the first step it is advantageous for a large surface of the sample carrier or sample region to be illuminated with such high intensity that a target object can be quickly identified, even with a relatively low microscopic magnification. However, high radiant power per unit area that is applied has the drawback that also the power of the scattered radiation is increased, whereby identification is made more difficult. Because the ratio between object radiation and scattered radiation is important for reliable target object identification, radiant power that is twice as high, for example, which is associated with twice the scattered radiation impinging on the camera, is not helpful.

In this regard, however, the invention is based on the deliberation that it is useful for expediting the method to select the illumination radiant power as high as possible, and to accept poor collimation of the illuminating radiation over focusing on the sample surface. However, it must prevented that a significant portion of the resulting strong scattered radiation reaches the camera. For example, an intermediate aperture assembly, advantageously comprising several intermediate apertures or diaphragms, in the field of view tube can significantly reduce the portion of scattered radiation. This can compensate for the drawback of poor collimation, at least to a significant degree.

High radiant power can be achieved by a large-area radiating element, such as an LED. According to a further advantageous embodiment of the invention, the second light source comprises a large-area radiating element. A particularly high excitation radiant power on the sample can thus be achieved.

So as to further increase the power, it is advantageous for the optical path between the light source and sample to be as short as possible. This is particularly important with large-area radiating elements, such as LED sources, which are difficult to collimate. The distance between the light source, for example an LED, and the sample carrier is advantageously less than 100 mm, and more particularly less than 50 mm.

The key in the second step is primarily to analyze the target object in a differentiated manner, and therefore the high radiant power from the first step is not necessarily required. A low scattered radiation rate is advantageous for the purpose of precise and differentiated diagnostics. According to the invention, the radiation of the second light source is thus collimated by the field of view tube and guided in particular coaxially relative to the optical axis. With sufficient radiant power, a good ratio between the sample radiation and scattered radiation can thus be achieved.

It is further advantageous for the power with which the sample is irradiated and which comes from the first light source to be at least three times as high per nm frequency range, and more particularly to be at least ten times as high, as the corresponding radiant power from the second light source. The entire overview field of view can thus be illuminated with such intensity that the radiant power per unit area is sufficient to generate sufficiently strong reflection of a single target object, so that the identification thereof is possible even with a lower microscope resolution.

In a further advantageous embodiment of the invention, all biological target objects to be found contain a general marker as a predetermined optical property, and the biological material is analyzed only for the general marker in the first step. An identification of individual cells in a large number of miscellaneous biological material is thus easy to do. In particular cell identification at a ratio of $10^7$, and more particularly of $10^8$, unmarked cells to each marked cells is possible expeditiously.

It is further advantageous for the biological target objects to also have a classification marker as a further optical property, and for the biological target objects to be analyzed for these in the second step. This allows a simple, differentiated analysis and classification.

In the first step, the biological target object is advantageously analyzed for the coordinates thereof on the sample carrier, and it is analyzed for target-specific properties at a higher optical magnification only in the second step. The coordinates may be two-dimensional coordinates, which are located in a surface area, notably perpendicular relative to the optical axis of the imaging radiation emitted by the sample. However, it is also possible to incorporate the third dimension in the ascertained coordinates, using special autofocus methods. However, in general the third dimension is not detected until the second step, for example using autofocus methods.

The target-specific properties are advantageously color and/or shape properties of the target object. Fluorescent and/or luminescent markers, staining, nanocoding or morphological properties are particularly suited for this purpose.

Especially with a large-volume sample, for example 7.5 ml blood containing approximately $5\times10^7$ bloodcells, it is advantageous to carry out a grid-shaped scan of a sample surface in the first step, the surface being larger than the overview field of view of the microscope optical system. It is thus proposed to sequentially scan, in the first step, a sample surface of the sample carrier by field of view, determine the position of the found target object in the overview region, and, in the second step, to individually move to the found target objects and microscopically analyze them. The overview region on the sample surface can correspond to the overview field of view of the microscope optical system in terms of size.

According to the invention, both the first and the second illumination units illuminate the material to be analyzed exclusively from one side. Access to the sample from the other side is thus maintained.

Advantageously both illumination units illuminate the sample or a sample carrier from beneath, wherein the sample remains accessible from above. The material to be analyzed can thus be easily modified. It is possible, for example, for a robot to add material to be analyzed or a different substance, such as an active ingredient, to the sample carrier, or remove it therefrom, during the microscopy method.

The invention is further directed to a microscope device for classifying labeled cells in the biological material, and more particularly for autonomously and automatically classifying them. The microscope device can be connected to a sample carrier and comprise a microscope optical system that is aligned with the sample carrier. The microscope device further contains a first illumination unit having a first light source, which comprises several illumination sources which are disposed outside a field of view tube in an annular manner around the field of view tube and which are aligned conically with the sample carrier. The two-step method described above can thus be carried out particularly expeditiously and reliably.

According to an advantageous embodiment of the invention, the microscope device comprises a second illumination unit for illuminating the sample carrier coaxially relative to the optical surface through the field of view tube. This second illumination unit does not need to contain a dedicated light source, because it may be sufficient to feed radiation from an external light source. In such an externally illuminated case, the illumination unit is composed of several light guide elements for guiding radiation from the external light source onto the sample carrier.

It is further proposed that the first light source comprise several illumination sources, which are collectively disposed in an annular shape around an objective of the microscope optical system. This allows a conical radiation guidance from the illumination sources onto the sample carrier or the biological material carried by the same, whereby high radiant power per unit area is made possible.

So as to achieve as high as possible a radiant power from the first illumination unit onto the sample carrier or the biological material located thereon, it is advantageous for each of the illumination sources to comprise an output optical system, wherein the output optical systems adjoin each other and surround the field of view tube in an annular manner. In this way, optimal radiant efficiency can be achieved from the illumination sources onto the sample carrier or the biological material.

It is further proposed for the microscope device to comprise a first filter unit having a first filter means which is disposed between the illumination sources and the sample carrier. Such a first filter means can be an excitation filter, which limits the radiation that is applied to the sample to a filter bandwidth which in particular does not exceed the range of 50 nm, and more particularly of 25 nm. A second filter means is advantageous, which is disposed in the optical beam path between an objective of the microscope optical system and the camera. Compared to the first filter means, this second filter means is advantageously designed so that it is only transmissive in a second spectral region, which is outside the spectral region in which the filter means is transmissive. This measure can also considerably reduces the scattered radiation incident on the camera.

So as to further reduce the scattered radiation, it is advantageous for several intermediate apertures or diaphragms to be disposed in the field of view tube, these diaphragms absorbing at least 90% of the scattered radiation that is emitted by the illumination sources of the first illumination unit and has passed through the objective.

The above description of advantageous embodiments of the invention contains numerous characteristics, some of which can be found combined with each other in the individual dependent claims. However, a person skilled in the art will advantageously also consider these characteristics individually and combine them into useful further combinations. These characteristics in particular can be combined individually and in any arbitrary suitable combination with the method according to the invention and the device according to the invention in accordance with the independent claims.

The properties, characteristics and advantages of the present invention as described above, and the manner in which these are achieved, will become more apparent and clearly understandable in connection with the following description of the exemplary embodiments, which will be described in more detail in connection with the drawings. The exemplary embodiments are intended to describe the invention and do not limit the invention to the combination of characteristics provided therein, to include with respect to functional characteristics. Moreover, suitable characteristics of each exemplary embodiment can also be considered explicitly on their own, taken out of an exemplary embodiment and introduced in another exemplary embodiment so as to supplement the same and/or combined with an independent claim.

Figure 1:
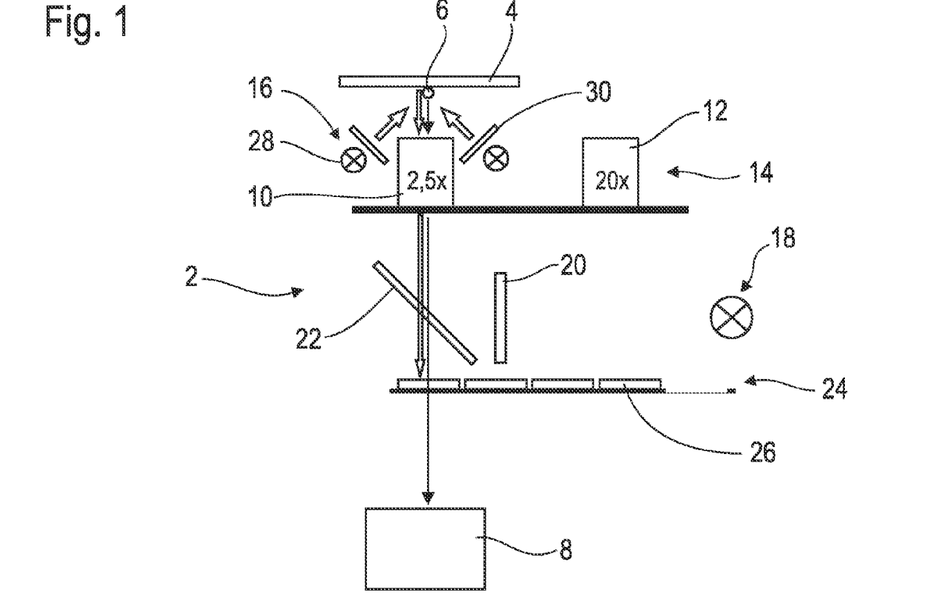
FIG. 1 shows a schematic drawing of a fluorescence microscope comprising two objectives and two illumination units during a rough scan.

FIG. 1 shows a microscope device 2 comprising a sample carrier 4 on which biological material 6 is arranged. The microscope device 2 comprises a camera 8 and two objectives 10, 12 having a magnification of 2.5 times and 20 times, which together form the microscope optical system 14. The microscope device 2 further comprises a first illumination unit 16, a second illumination unit 18 having a spectral filter 20, a beam splitter 22 and a spectral filter unit 24 having a plurality of spectral filters 26. The first illumination unit 16 comprises a plurality of illumination sources 28, each having a spectral filter 30.

A microscopy method for identifying biological target objects 32 in the biological material 6 will be described hereafter in detail based on FIGS. 1 to 7.

First, the sample carrier 4 is positioned in front of the first objective 10 of the microscope device 2 for the analysis. The sample carrier 4 is a micro-plate containing, for example, 8×12 vessels 34, in each of which a predetermined quantity of body fluid is introduced. For the analysis for tumor cells, for example, 1.5 ml blood is distributed among the 96 vessels 26, so that 5 micro-plates yield a representative analysis quantity of 7.5 ml of blood.

The biological material 6 contains approximately $10^7$ cells in the sample carrier 4, some of which can be individual tumor cells. The object of the method is that of determining whether tumor cells are present in the biological material and if so, to classify these, with multiple categories or classes being differentiated. The tumor cells thus form biological target objects 32 which are to be identified. The biological material 6 is bound to the bases of the vessels 34 in a layer, with clusters and optionally smaller overlaps of cells being possible. The cells are thus held in the vessels 34 in a stationary manner and do not change the positions thereof within the vessels 34 during the analysis.

So as to be able to find and differentiate the tumor cells, the biological material 6 has undergone a labeling procedure, whereby cells with certain receptors are labeled with corresponding markers, for example fluorescent markers. One of the markers is a general marker, which adheres to all target objects 32 to be found, these being tumor cells in the present exemplary embodiment. The other markers are differentiation markers, which are assigned to target object classes, so that all target objects of one class carry one of the differentiation markers. The general marker has an excitation frequency of 488 nm and an emission frequency of 510 nm. The differentiation markers have an excitation frequency of 375 nm, 405 nm, 550 nm and 649 nm.

Figure 2:
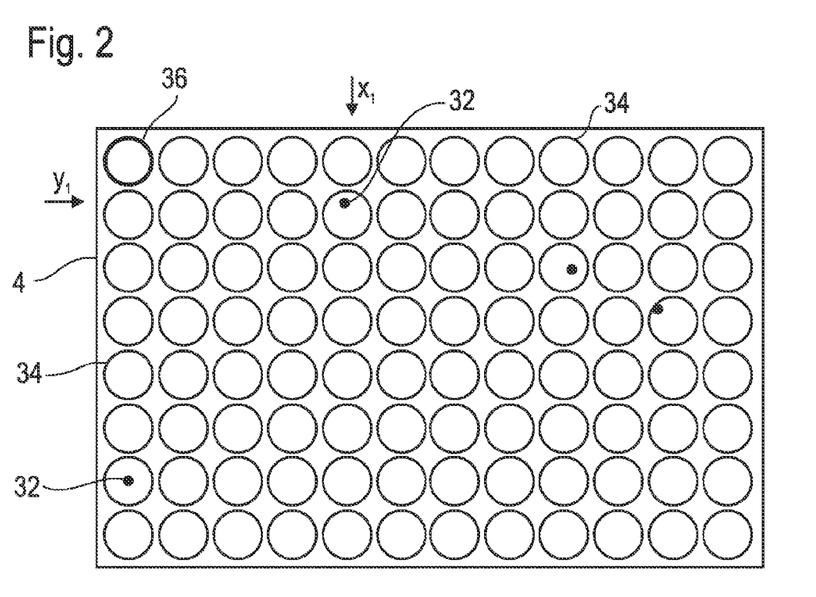
FIG. 2 is a top view of a sample carrier containing many sample vessels.

In the first step of the exemplary method, an overview field of view 36 of the first objective 10 is directed to the biological material 6 on the sample carrier 4 so that an overview region of the sample carrier 4 or of the biological material 6 is imaged in the camera 8. The overview field of view 36 indicated in FIG. 2 is selected large enough for the content of a vessel 34 to be located entirely within the overview field of view 36, whereby the biological material 6 located therein can be fully imaged in the camera 8. On the other hand, the size and position of the overview field of view 36 are selected such that an upper edge of the rim of the vessel 34 is not located in this overview field of view and thus is not imaged.

The overview field of view 36 is now illuminated by the first illumination unit 16. The first illumination unit 16 contains a plurality of illumination sources 28 for this purpose, in the present exemplary embodiment there are ten, which are disposed in a circle around the objective 10.

Figure 3:
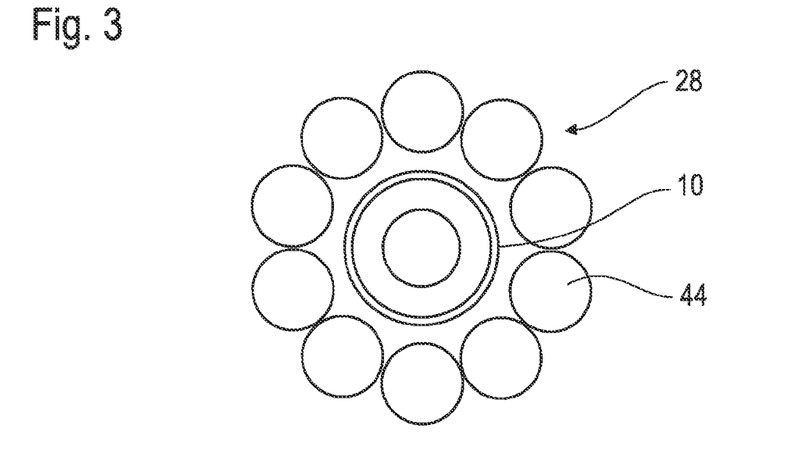
FIG. 3 is a schematic illustration of the second illumination unit which is disposed around a microscope objective.
Figure 4:
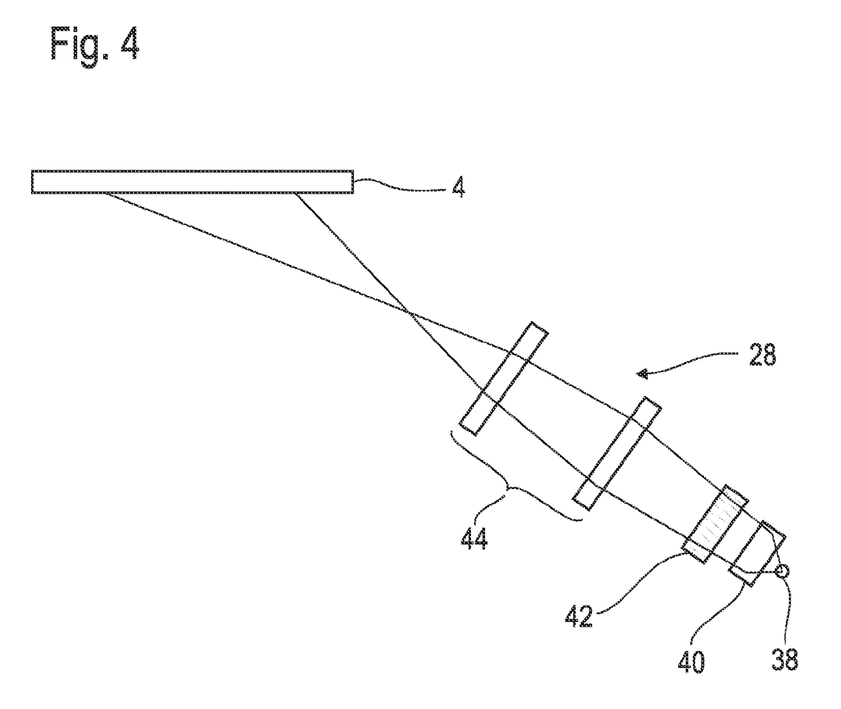
FIG. 4 shows an illumination source of the second illumination unit.

A view from above onto the objective 10 and the first illumination unit 16 is shown schematically in FIG. 3. FIG. 4 is a representation of an illumination source 28. Each illumination source 28 comprises a light source 38, in this exemplary embodiment one or more LED radiating elements, a collimation optical system 40, for example a collimation lens, an emission filter 42, which can be a spectral filter having a single transmission band, which advantageously has a width σ<50 nm, and an output optical system 44, which in the present exemplary embodiment is a refocusing optical system made of two lenses. The illumination sources 28 are placed around the objective 10 for this purpose such that the output optical systems 44 thereof form a substantially uninterrupted ring around the objective, with frames for the output optical systems 44 and minor play between these being insignificant.

Each of the illumination sources 28 radiates obliquely onto the sample carrier 44 and collectively they form a beam cone, which converges on the sample carrier 4 in an illumination surface that is directed to the objective 10. This illumination surface area is exposed to monochrome illumination jointly by the illumination sources 28. The spectral filtration for this is achieved by the emission filters 42, which in the present exemplary embodiment allow a spectral band having the width of σ<20 nm to pass from the radiation spectrum of the illumination sources 28 and do not allow the remaining radiation from the illumination sources 28 to pass. The focus of this excitation band, and advantageously the entire band, is located in a higher frequency range than the excitation frequency of the general marker. In addition, the entire excitation band is in the non-transmissive frequency range of both the beam splitter 22 and of the filer 26.

Because of the strong illumination of the biological marker in the excitation band of the general marker, the marker reflects in an emission band which in the present exemplary embodiment is around 510 nm. The radiation of each biological target object tagged with the general marker is so strong that it is detected by the camera 8. The camera 8 may contain a detection means for this purpose, for example an image recording unit. Hereinafter, a detection means and a differentiation means are associated with the camera 8 to simplify matters So as to identify all target objects in all vessels 34 on the sample carrier 4, all possible regions of the sample carrier 4 in which a target object may be located, which in the present exemplary embodiment are all vessels 34, are consecutively scanned. For this purpose, the overview field of view is consecutively directed to all vessels 34 and remains there for a predetermined duration, which in the present exemplary embodiment is approximately 500 ms. Thereafter, the overview field of view 36 is positioned on the next vessel 36 and the radiation in the excitation band emitted by the biological material is again detected. Including the positioning times of the overview field of view 36, such a detection process in the present exemplary embodiment takes approximately one minute and is carried out automatically, without requiring any intervention by the operator.

Each object radiating in the emission band at an intensity above a threshold value is detected by the camera 8 as a target object 32. For each target object 32, the position thereof in the overview field of view 36 is determined, and on this basis a position on the sample carrier is determined, because the position of the overview field of view 36 on the sample carrier 4 is known from a corresponding positioning means of the camera 8. The position is output in two-dimensional coordinates $x_i$, $y_i$. The position of the first target object 32 that is found is indicated in FIG. 2 accordingly with $x_1$, $y_1$. Four target objects 32 are present on the sample carrier 4 of FIG. 2, which are all found.

Because of the extremely strong illumination of the biological material 6, the same emits a lot of scattered radiation 46, which makes it more difficult to identify the target objects 32. Using a plurality of measures, this scattered radiation 46 is reduced to such a degree that reliable identification of the target objects is not jeopardized.

As a first measure, the sample surface is illuminated by the first illumination unit 16 from outside the objective 10. The illumination radiation thus irradiates the sample carrier 4 at a different angle than that at which the field of view of the camera 8 is directed to the sample carrier 4. In the exemplary embodiment of FIG. 1, the illumination angle is 45°, for example, wherein the field of view of the camera 8 is directed to the sample carrier 4 at an angle of 90°. Advantageously a difference of at least 30° exists between the illumination angle and the angle of view. This measure achieves that radiation which is reflected by the sample carrier 4 is not incident, or is incident only insignificantly, on the objective in the direction of view of the camera 8.

Figure 5:
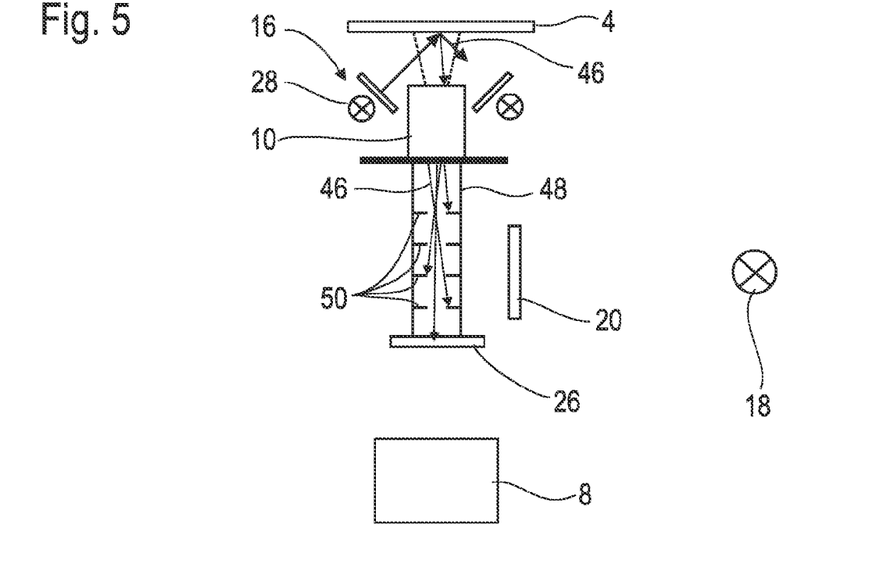
FIG. 5 shows an optical path of scattered radiation which is emitted by a sample and largely absorbed in a field of view tube.

This is indicated in FIG. 5. Scattered radiation 46 reflected by the sample surface is reflected past the objective 10. Only scattered radiation that emanates from curved surfaces of the biological material due to multiple scattering or minor scattering reaches the objective 10, as is indicated in FIG. 5. However, the majority of this scattered radiation is not collimated and does not run in the direction of view of the camera 8.

So as to prevent this scattered radiation 46 from entering the camera, the microscope device 2 comprises a field of view tube 48 between the objective 10 and the camera 8, the tube having a length of approximately 10 cm. A plurality of apertures 50 are disposed inside this field of view tube 48, which absorb uncollimated radiation. At least 90% of scattered radiation 46 entering the objective 10 is thus not allowed to pass.

This measure of blocking uncollimated scattered radiation 46 achieves the further advantage that scattered radiation 46 that is still able to pass the collimating apertures 50 is largely collimated, so that it impinges perpendicularly on the downstream spectral filter 26. In this radiation direction, the filtration action of the spectral filter 26 is optimal, so that it substantially filters out the scattered radiation 46.

Despite very high incident light on the sample surface, it can thus be reliably achieved that the scattered radiation is so low that it does not significantly interfere with a reliable identification of even individual target objects 32 in the large overview field of view 36.

Figure 6:
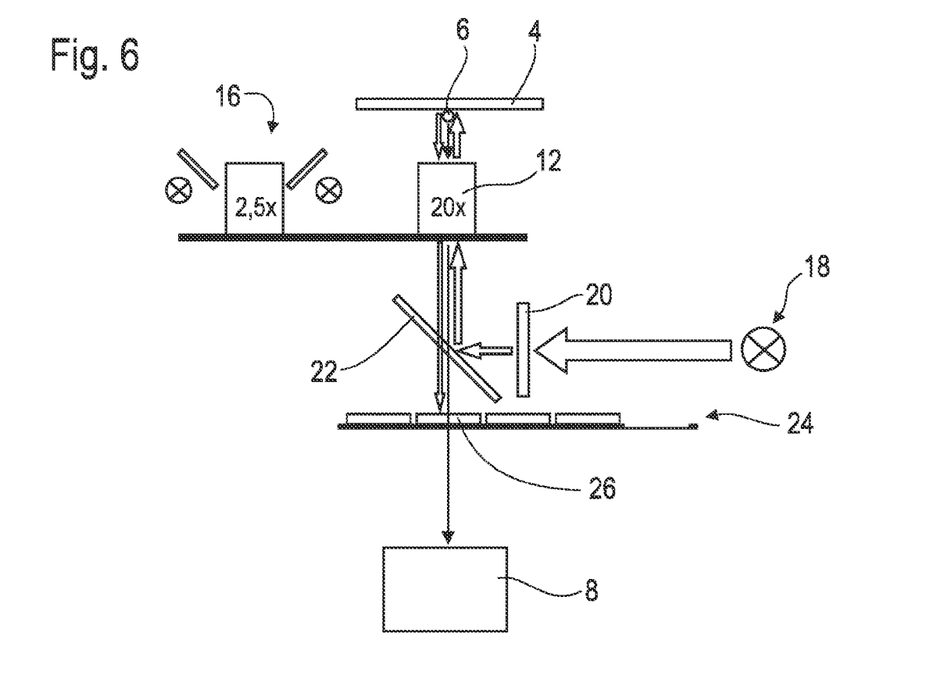
FIG. 6 shows the fluorescence microscope during a detailed analysis.
Figure 7:
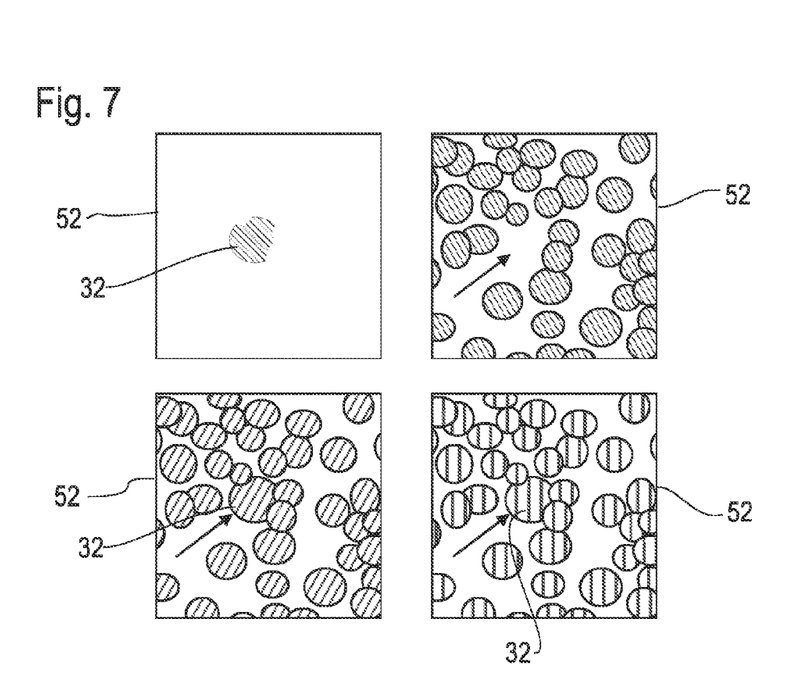
FIG. 7 is a target field of view around one of the biological target objects at four different illuminations.

When the entire sample surface is scanned and the positions of all target objects 32 have been recorded, the second step of the method is carried out. For this purpose, the microscope optical system 14 is switched over, so that the second objective 12 is used. This is shown in FIG. 6. The objective 12 has 20-fold magnification and thus images a smaller target field of view 52 onto the camera 8, which is shown in FIG. 7. Based on the stored two-dimensional positions of the detected target objects 32, the target field of view 52 is now consecutively aligned with these target objects 32. The target objects are then analyzed for additional optical properties, which advantageously differ from the optical property of the general marker.

For this purpose, the sample carrier 4 is illuminated by the second illumination unit 18 in the region of the target field of view 52. However, contrary to the first illumination unit 16, the second illumination unit 18 emits a continuous spectrum so as to provide a plurality of excitation bands in various frequency ranges. As an alternative, an illumination unit that provides each of the desired excitation bands in the various frequency ranges in monochrome form would be possible, so that contrary to continuous polychrome radiation now discrete polychrome radiation is made available.

The illumination radiation from the second illumination unit 18 is spectrally filtered in the excitation filter 20, wherein in the present exemplary embodiment polychrome illumination of the sample carrier 4 is allowed. As an alternative, alternating monochrome illumination using respective alternating excitation filters 20 is possible. Independently of these illumination variants, the radiation emitted by the sample is consecutively filtered in the filter unit 24 using a plurality of emission frequencies, wherein a plurality of filters 26 having differing transmission bands are used consecutively by introducing the filters consecutively in the imaging beam path. As an alternative, it is possible to allow a plurality of emission frequencies—in keeping with the markers that are used—to pass jointly to the camera 8 and to detect them, wherein the camera then has to be a color camera containing a color detector or containing a plurality of monochrome detectors.

The illumination radiation of the second illumination unit 18 is guided through the field of view tube 48 and the second objective 12 and reaches the sample parallel to the optical axis of the objective 12 and direction of view of the camera 8 onto the sample. Scattered radiation 46 that is reflected directly by the sample carrier 4 is thus also captured in the objective and is absorbed to a lesser degree by the apertures 50 in the field of view tube 48 than the scattered radiation 46 from the first illumination unit 16. While this scattered radiation 46 impinges perpendicularly on the filter 26 and is optimally filtered, nonetheless a higher content of scattered radiation per detected sample surface remains in the image than in the first step and with the illumination by the first illumination unit 16. However, the emission of the target object 32 is greater because of the higher magnification, so that the higher scattered radiation 46 does not considerably interfere with the differentiated analysis of the target object 32 in the second step.

FIG. 7 shows four target fields of vision 52, in which the biological material 6 located therein is illuminated with four different frequencies or analyzed on four different frequencies. These images of the four target fields of vision 52 are not taken and stored simultaneously, but consecutively.

In the exemplary embodiment shown in FIG. 7, a target object 32 is analyzed for several different optical properties, which due to corresponding staining or markers allow a conclusion of the biological properties of the target object 32. In the first target field of view 52, for example, the emission of FITC (fluorescein isothiocyanate) is detected, which is coupled to an immunoglobulin, in this case Anti-Cytokeratin. Because of this cytoplasmic staining, a large cell 32 having a specific antigenic surface property becomes visible.

In the second target field of view 52, the emission of phycoerythrin is detected, which has an emission peak at 575±10 nm and is bound to anti-CD45. This dye generates a mononuclear cell surface stain and in this bond is a marker that indicates a normal cell nucleus. It is apparent that in this target field of view 52 of the camera 8 many blood cells are visible, but the target object 32 does not appear. The cytoplasmic staining in the first target field of view 52 and the non-appearance in the mononuclear cell surface staining in the second target field of view 52 are indicators that the target object 32 is a circulating tumor cell. However, certainty is only obtained by additional markers.

In the third target field of view 52, the analysis is thus conducted for DAPI (4',6-diamidino-2-phenylindole) with an emission at 461 nm. DAPI is a cell nucleus marker which renders DNA properties of the nucleus visible. Together with the above-described markers, the nucleus marker of the target field of view appearing in the third target field of view 52 allows the conclusion that a tumor cell is present in the target object 32.

In the fourth target field of view 52, the filter unit 24 does not filter, as is indicated in FIGS. 1 and 6 in the filter field on the far right, whereby a bright field image is created. This image can be used for further analyses, for example a differentiation according to morphological properties.

So as to be able to uniquely localize the target object 32 in all target fields of vision 52 and distinguish it from other imaged objects, again the position of the target object 32 known from the first step is used, which differs from that of surrounding objects, for example surrounding cells. The target object 32 detected in the first step is thus automatically analyzed in the second step for a series of optical properties, based on which the target object 32 can be classified. For example, the target object 32 of FIG. 7 can be classified as a tumor cell. If one of the tested optical properties is different, the classification turns out differently.

In the above-described method, the same optical method, for example fluorescence analysis, can be employed in both steps, which is to say both for identifying the target objects 32 and for the differentiating analysis thereof for classification. However, it is also possible to select a different optical method in the second step, which allows a desired classification in a simpler way than the first method. Bright field microscopy has already been mentioned, wherein dark field microscopy or other methods are similarly possible.

One example of different methods will be described hereafter based on the illustration shown in FIG. 8. In the first step, biological material 6 which has been labeled with one or more stains is analyzed by means of fluorescence analysis. For example, certain bacteria are being searched for as the target objects 32, which are labeled accordingly. The target objects and the positions thereof are detected in the first step, as described above.

In the second step, the biological material 6 is again imaged with the target field of view 52 onto the camera 8. FIG. 8 shows the target field of view 52 having an identical position at five different times $t_1$-$t_5$. For the sake of simplicity, only one bacterium is shown as the target object 32, wherein other objects can also be imaged, without interfering with the analysis described hereafter, because the position of the target object 32 has been detected with sufficient precision to distinguish it from the remaining imaged objects.

At the first time $t_1$, the target object 32 is analyzed for morphological properties. This can be done directly by means of image processing or indirectly by way of radiated quantities. For example in dark field microscopy, the detected radiated quantity can be dependent on the size of the target object 32 in the target field of view. If the target object 32 grows, the radiation thereof increases, and the growth can be detected indirectly by way of the received radiant power.

Figure 8:
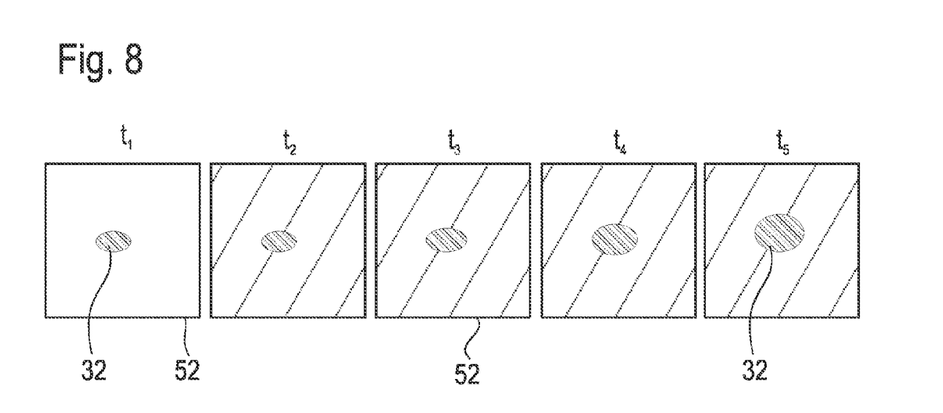
FIG. 8 is a target field of view which is directed to a bacterium, at five different times.

An active ingredient is added to the target object 32 before the second time $t_2$, which is indicated in FIG. 8 by the hatching. It is to be tested how the target object 32 develops under the effects of the active ingredient. For this purpose, in the second step the target object 32 is analyzed as a function of the time and classified as a function of this analysis. In the example shown in FIG. 8, the bacterium grows over time, so that a corresponding interaction with the active ingredient can be concluded. The target object 32 is classified accordingly.

Another analysis example will be described based on the illustration of FIG. 9. The sample carrier 4 contains a plurality of what are known as nanocodes, these being small carrier units 54, each having a machine-readable code, such as a bar code or another code. In the exemplary embodiment shown in FIG. 9, the code is composed of dots and lines, the arrangement of which relative to each other results in a predetermined content, for example a number. Each carrier unit 54 additionally contains a sample surface 56, on which the biological material is bound, optionally together with a marker. The biological material can thus be connected to the code, so that each of the carrier units 54 can carry different biological material or differently labeled biological material, which can be distinguished based on the code.

Figure 9:
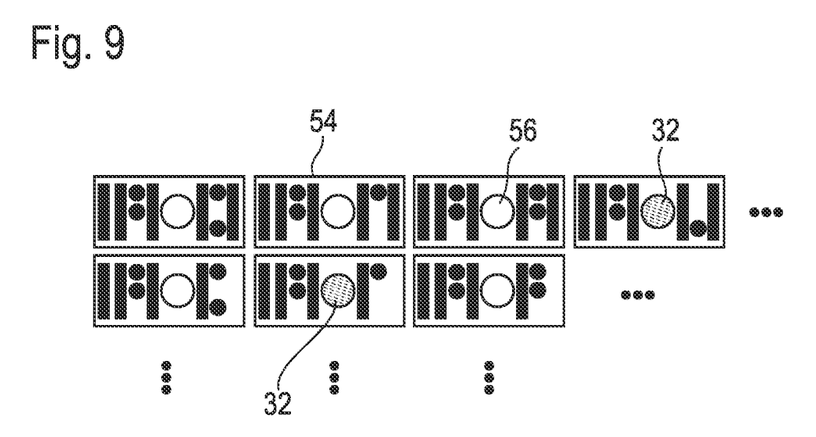
FIG. 9 is an overview field of view which is directed to a plurality of nanocodes.

In the first step, a large number of the carrier units 45 are jointly imaged in the overview field of view, as is indicated in FIG. 9. Depending on the presence of markers in the biological material, the sample surfaces 56 will differ in the emission thereof, so that the searched-for marker, and thus the searched-for biological material, can be found as the target objects 32. The biological target objects 32 can be the carrier units 54, the sample surfaces 56 thereof of the corresponding biological material.

The code of at least those nanocodes which carry or form the detected target objects 32 is also read in the first step. The target objects can thus be associated with a code, and thus with additional information, already in the first step. Optionally a classification into various classes is already possible in the first step.

In the second step, an optical analysis having a higher magnification takes place, similarly as described above. The target objects 32 can be analyzed in any arbitrary manner for this purpose, for example by means of fluorescence analysis, dark field analysis or the like. In accordance with the further optical properties, the target objects 32 are automatically classified.

LIST OF REFERENCE NUMERALS 2 microscope device
4 sample carrier
6 biological material
8 camera
10 objective
12 objective
14 microscope optical system
16 illumination unit
17 illumination unit
20 filter
22 beam splitter
24 filter unit
26 filter
28 illumination source
30 filter
32 biological target objects
34 vessel
36 overview field of view
38 light source
40 collimation optical system
42 emission filter
44 output optical system
46 scattered radiation
48 field of view tube
50 aperture
52 target field of view
54 carrier unit

The invention claimed is:

1. A microscopy method for identifying target objects (32) in material (6) to be analyzed, the target objects (32) having a predetermined optical property, wherein
in a first step, an overview field of view (36) of a microscope optical system (14) is directed to an overview region of a sample carrier (4) containing the material (6) to be analyzed;
the material (6) to be analyzed is illuminated by an illumination unit (16), which irradiates the sample carrier (4) from outside a field of view tube (48), and is recorded by a camera (8);
the material (6) to be analyzed is optically analyzed for the optical property such that even a single target object (32) having the predetermined optical property is identified as such in the material (6) to be analyzed;
in a subsequent second step, a target field of view (52) of the microscope optical system (14) is aligned with a target region around the target object (32) using the known position of the target object (32); and
the identified target object (32) is analyzed in a manner differentiated for various additional optical properties.

2. The microscopy method according to claim 1, characterized in that the target field of view (52) has a magnification by at least a factor of 3 over the overview field of view (36).

3. The microscopy method according to claim 1, characterized in that the identification of the target object (32) in the first step is carried out with a first optical method and the differentiation of the target object (32) in the second step is carried out with a second optical method which is different from the first.

4. The microscopy method according to claim 1, characterized in that, in the second step, the material (6) to be analyzed is illuminated by a second and different illumination unit (18), which allows the target objects (32) to be differentiated for various further optical properties by illumination at different frequencies.

5. The microscopy method according to claim 4, characterized in that the illumination by the first illumination unit (16) takes place with LED light and the second illumination unit (18) comprised a radiating element having a continuous spectrum.

6. The microscopy method according to claim 4, characterized in that, in the second step, the material (6) to be analyzed is illuminated by the second and different illumination unit (18), which irradiates the sample carrier through the field of view tube (48) coaxially relative to the optical axis, and the first illumination unit (16) irradiates the sample at a power per nanometer of frequency range that is at least 5 times that of the second illumination unit (18).

7. The microscopy method according to claim 4, characterized in that both the first and the second illumination units (16, 18) illuminate the material (6) to be analyzed exclusively from one side.

8. The microscopy method according to claim 1, characterized in that all target objects (32) to be found have a general marker as a predetermined optical property and, in the first step, the material to be analyzed is only analyzed for the general marker, and the target objects (32) further have a classification marker as a further optical property and are analyzed for the same in the second step.

9. The microscopy method according to claim 1, characterized in that, in the first step, the target object (32) is analyzed for the coordinates thereof on the sample carrier (4) and is analyzed for target-specific properties at a higher optical magnification only in the second step.

10. The microscopy method according to claim 9, characterized in that the target-specific properties are color and/or shape properties of the target object.

11. The microscopy method according to claim 1, characterized in that in the second step the development over time of at least one property of the found target objects (32) is analyzed.

12. The microscopy method according to claim 1, characterized in that, in the first step, a sample surface of the sample carrier (4) is sequentially scanned by field of view, the position of the found target object (32) in the overview region is determined, and in the second step the found target objects (32) are approached individually and analyzed microscopically.

13. A microscope device (2) for classifying target objects (32) in material (6) to be analyzed, comprising a sample carrier (4), a microscope optical system (14) that is oriented to the sample carrier (4), a first illumination unit (16) having a plurality of illumination sources (28), which are disposed outside a field of view tube (48) in an annular manner around the field of view tube (48) and which are aligned conically with the sample carrier (4).

14. The microscope device (2) according to claim 13, characterized by a second illumination unit (18) for illuminating the sample carrier (4) with an illumination beam path that is guided coaxially relative to the optical axis through the field of view tube (48).

15. The microscope device (2) according to claim 14, characterized in that each of the illumination sources (28) has an output optical system (44), the systems adjoining each other and surrounding the field of view tube (48) in an annular manner.

16. The microscope device (2) according to claim 14, characterized by a filter unit, comprising a first filter means (20, 30), which is disposed between the illumination sources (16, 18) and the sample carrier (4), and a second filter means (22, 24), which is disposed in the optical beam path between an objective (10, 12) of the microscope optical system (14) and the camera (8), the first filter means (20, 30) being only transmissive in a first spectral region and the second filter means (22, 24) being only transmissive in a second spectral region outside the first spectral region.

17. The microscope device (2) according to claim 13, characterized in that a plurality of intermediate apertures (50) are disposed in the field of view tube (48), which absorb at least 70% of the uncollimated scattered radiation (46) of the first illumination source (16) that has penetrated from the sample carrier (4) into the field of view tube (48).

* * * * *